(12) United States Patent
Schafer et al.

(10) Patent No.: US 9,271,489 B2
(45) Date of Patent: Mar. 1, 2016

(54) CARBONATE ESTER TUBER TREATMENT COMPOSITION

(71) Applicant: ACETO AGRICULTURAL CHEMICAL CORPORATION, Port Washington, NY (US)

(72) Inventors: Ron Schafer, Boise, ID (US); Terry Kippley, Northport, NY (US)

(73) Assignee: ACETO AGRICULTURAL CHEMICAL CORPORATION, Port Washington, NY (US)

( * ) Notice: Subject to any disclaimer, the term of this patent is extended or adjusted under 35 U.S.C. 154(b) by 0 days.

(21) Appl. No.: 14/514,880

(22) Filed: Oct. 15, 2014

(65) Prior Publication Data

US 2015/0264919 A1    Sep. 24, 2015

Related U.S. Application Data

(60) Provisional application No. 61/968,185, filed on Mar. 20, 2014.

(51) Int. Cl.
| | |
|---|---|
| *A01N 43/58* | (2006.01) |
| *A01N 43/02* | (2006.01) |
| *A01N 25/02* | (2006.01) |
| *A01N 47/20* | (2006.01) |
| *A01N 37/10* | (2006.01) |
| *A01N 37/12* | (2006.01) |
| *A01N 43/08* | (2006.01) |

(52) U.S. Cl.
CPC ............... *A01N 25/02* (2013.01); *A01N 37/10* (2013.01); *A01N 37/12* (2013.01); *A01N 43/08* (2013.01); *A01N 47/20* (2013.01)

(58) Field of Classification Search
None
See application file for complete search history.

(56) References Cited

U.S. PATENT DOCUMENTS

| | | | |
|---|---|---|---|
| 8,329,618 | B1 | 12/2012 | Schafer et al. |
| 2007/0027033 | A1 | 2/2007 | Sardo |
| 2007/0135307 | A1 | 6/2007 | Olson et al. |
| 2008/0300313 | A1 | 12/2008 | Byrne et al. |

OTHER PUBLICATIONS

U.S. Appl. No. 13/615,900, filed Sep. 14, 2012, Schafer, et al.
International Search Report issued Jan. 2, 2015 in PCT/US14/61354.
Written Opinion issued Jan. 2, 2015 in PCT/US14/61354 (with Search History).
European Office Action issued Sep. 28, 2015 in Patent Application No. 15159009.8.

*Primary Examiner* — Alton Pryor
(74) *Attorney, Agent, or Firm* — Oblon, McClelland, Maier & Neustadt, L.L.P.

(57) ABSTRACT

A carbonate ester composition containing at least one carbonate ester, preferably an alkylene carbonate, and a sprout inhibitor. A tuber having, on at least a part of a surface thereof, the disclosed carbonate ester composition. A method of applying the carbonate ester composition onto the surface of a tuber. A method of applying a carbonate ester composition onto the surface of a potato tuber.

13 Claims, 1 Drawing Sheet

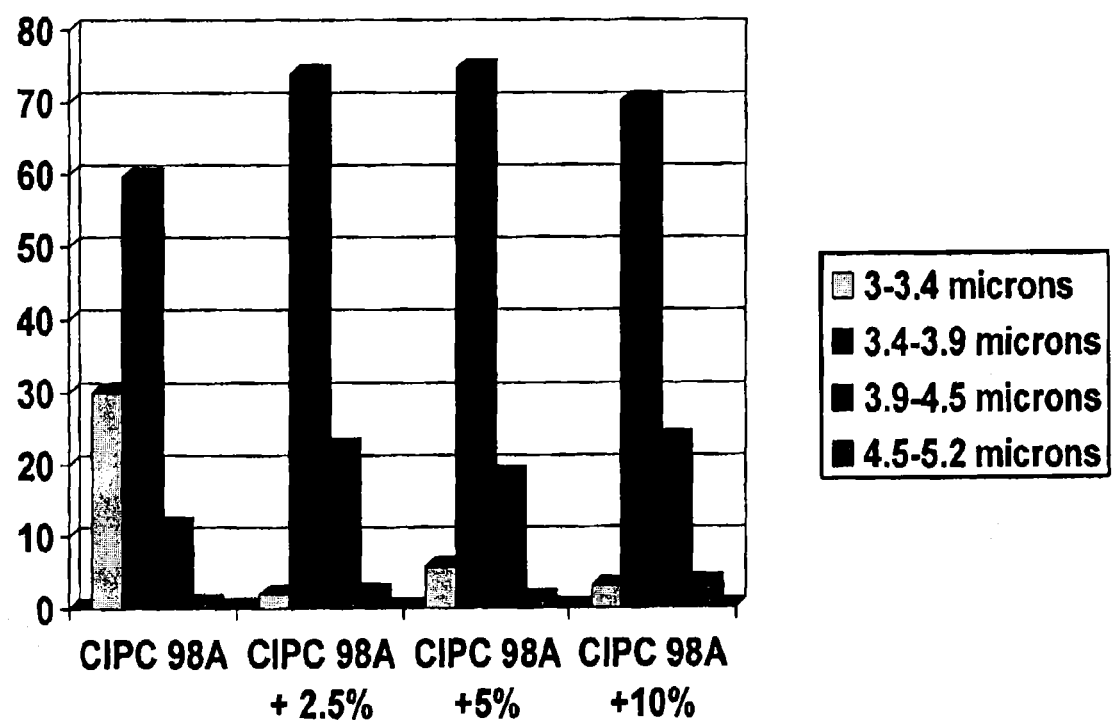

CARBONATE ESTER TUBER TREATMENT COMPOSITION

FIELD OF THE INVENTION

The present invention relates to the use of a composition of a compound having sprout-inhibiting properties with carbonate ester(s) to treat tubers and/or bulbs, for example to accomplish one or more of the following: to burn back existing bud and/or sprout tissue, to inhibit sprouting of tubers, to reduce shrinkage, to maintain tuber quality and weight, to maintain firmness and turgidity, etc. The application of this composition to tubers and/or bulbs also makes up a part of the invention, especially "on the line," as do tubers and/or bulbs having this composition on at least a part of a surface thereof. Because potatoes are an important application of the present invention, they will be discussed in detail below. However, the invention is not limited thereto, and the invention includes the treatment, etc., of tubers in general such as other root crops like sweet potatoes and yams, and bulbs like onions, etc.

BACKGROUND OF THE INVENTION

It is well known in the art to treat tubers such as potatoes with various chemicals having sprout-inhibiting properties. CIPC (chlorpropham, chlorprophame; chlor-IPC IUPAC name isopropyl 3-chlorocarbanilate; isopropyl 3-chlorophenylcarbamate; Chemical Abstracts name 1-methylethyl (3-chlorophenyl)carbamate EEC no. 202-925-7) has been conventionally used for this purpose for about 40 plus years. More recently, chemicals such as various isomers of diisopropylnaphalene and other substituted naphthalenes have exhibited for their sprout-inhibiting characteristics.

Potato tubers are often treated with a chemical sprout inhibitor in the storage season, and may receive another treatment of sprout inhibitor before being packaged for shipment to retail outlets. In the absence of chemical sprout inhibitors, the ultimate storage life is greatly reduced by loss of dormancy and early sprouting. Thus, virtually all potatoes stored mid and long term are treated with chemical sprout inhibitors.

Potatoes when being dug are frequently bruised, cut and/or abraded. These injuries to the potatoes oftentimes cause spoilage during shipment, storage and the like. A process known as suberization occurs naturally which tends to heal many of these injuries. However, whenever potatoes are stored, which occurs with a particularly large portion of potatoes harvested in any given year, if healing occurs slowly, a significant loss of potatoes can occur through spoilage. Early treatment with certain sprout inhibitors, such as CIPC, may retard the suberization process, thus contributing to the loss of potatoes through spoilage.

The main sprout inhibitors registered for use on potatoes are (CIPC), maleic hydrazide (MH), dimethylnaphthalene (DMN), 3-decen-2-one, and diisopropylnaphthalene (DIPN). The two chemicals in combination (CIPC plus DIPN) appear to be more effective at lower concentrations than either of the two chemicals alone. Simultaneous application of CIPC and DIPN provides improved results over application of either sprout inhibitors separately.

For example, it is relatively common in the potato storage industry to treat potatoes with Chloroisopropyl-N-carbamate (CIPC) to prevent or retard development of sprouts in the potatoes. Even though untreated potatoes are stored at a cool temperature, for example, generally between about 36-52° F., sprouting does begin to occur after a month or more of storage. Storage of upwards of six to ten months is typical for stored potatoes. Thus, without treatment of a chemical such as CIPC, the stored potatoes become entangled in sprouts and the whole stored lot of potatoes may become economically useless. Although early treatment with CIPC could be advantageous for sprout inhibition purposes, application of CIPC is typically delayed until after suberization has occurred inasmuch as CIPC tends to retard suberization, resulting in accelerated rot and spoilage.

CIPC is typically applied in one or multiple applications to the tubers to be stored using thermal fogging techniques, sprays and powders. Conventional thermal fogging involving the application of CIPC into a stream of hot air or onto a hot surface of 500-1000° F., to produce a CIPC aerosol. The CIPC aerosol is circulated through potatoes piled in a potato storage building with the use of fans. CIPC residue levels, will, however, typically decrease over time due to biodegradation. To extend the effective sprout inhibiting capability of CIPC, further applications may be needed.

CIPC is used in significant quantities world wide and is capable of suppressing sprouts on stored tubers with the chemical ability to limit cell division. Increased rates, multiple applications, addition of substituted naphthalene chemistries coupled with strict storage management strategies have been implemented to help reduce sprout development in CIPC treated potatoes. Yet the tubers often develop swollen white bud tissue and small peeping sprouts that are undesirable and when present can reduce the fresh pack potato value from 50% to 100% (complete rejection) at the point of delivery. The high polarity of carbonate esters provides excellent solubility properties for sprout inhibition compounds. In addition, the high boiling point of carbonate esters imparts non-flammable properties which make them well suited for both large and hot fogging machines. The instant invention provides, among other things, an effective treatment protocol that darkens and/or burns back these unwanted buds and small sprouts and allows the potatoes to be wholly valued in the market. In addition, the formulation provides a smaller distribution of particle size of the vapor molecules produced. It also provides assurance of less shrinkage (weight loss) and maintains the tuber quality.

Further, the formulation is not flammable which provides improved effects over the traditional flammable formulations. The formulation has a low flash point and a low temperature stability which are very valuable attributes for a liquid, especially during transportation and storage.

BRIEF DESCRIPTION OF THE DRAWING

FIG. 1 is a graph showing a shift in particle size distribution when 0, 2.5, 5 and 10% of propylene carbonate is added to a CIPC product.

DETAILED DESCRIPTION OF THE PREFERRED EMBODIMENTS

The present invention related to a carbonate ester formulation and to the use of carbonate ester(s) as a solvent for chemicals having sprout inhibiting properties. The carbonate ester(s) may be combined with one or more sprout inhibitors, such as CIPC, DMN and DIPN to form a carbonate ester formulation. The application of the carbonate ester formulation to tubers and/or bulbs also makes up a part of the invention, both alone and in any combination (physical, sequential, etc.), as do tubers and/or bulbs having one or more carbonate ester(s) or carbonate ester formulations on at least a part of a surface thereof. The tubers and/or bulbs treated according to the invention may be in any stage of their "lifecycle" (natural and commercial) when the inventive carbonate ester formulation is applied thereto.

The carbonate ester(s) which can be used herein include preferably alkylene carbonates. These carbonates have a high liquid temperature range and thus are low in flammability. They are also highly polar. The carbonate esters can be for example

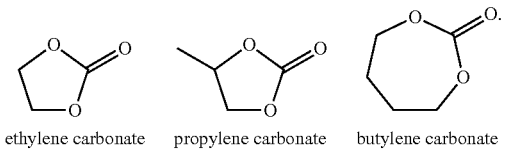

ethylene carbonate   propylene carbonate   butylene carbonate

Mixtures of the above compounds may also be used.

The carbonate esters are contained in the formulation in an amount of from 10% to 99%, preferably from 20 to 90%, preferably from 30 to 80%, preferably from 40 to 70%, preferably from 40 to 60%, preferably from 45 to 55%, and all ranges and sub ranges there between, based on the total weight of the formulation. The sprout inhibitor is contained in the formulation in an amount of from 1% to 90%, preferably from 10 to 80%, preferably from 20 to 70%, preferably from 30 to 60%, preferably from 40 to 60%, preferably from 45 to 55%, and all ranges and sub ranges there between, based on the total weight of the formulation.

The carbonate ester formulation preferably does not contain alcohol.

The carbonate ester may be added to the sprout inhibitor simultaneously or sequentially.

The formulation may be applied to the tubers to be stored using thermal fogging techniques. Conventional thermal fogging involving the application of CIPC into a stream of hot air or onto a hot surface of 500-1000° F., to produce a CIPC aerosol. The CIPC aerosol is circulated through potatoes piled in a potato storage building with the use of fans.

The temperature of the carbonate ester may be from 1° C. to 240° C., preferable 10° C., 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200, 210° C., 220° C., and 230° C. and all values and sub-ranges therebetween, before and/or during application to the potatoes. The carbonate ester formulation may be heated once or multiple times before application. The heating may be conducted during any of the mentioned application processes.

As used herein, the term "tuber" is inclusive of "potato tuber." "Potato tuber" refers to the underground storage organ of the potato plant (*Solanum tuberosum*). The potato tuber is a modified stem and includes buds that can sprout and form new potato plants. The term "(potato) tubers" refers to both tubers generally and to potato tubers of various varieties. Preferred potatoes include Russet Burbank, Ranger Russet, Umatilla Russet, Shepody, Norkotah Russet, Yukon Gold, Norchip, Gem Russet, Atlantic, Chipeta, Snowden, Meris Piper, king Edward, Desiree, Atlantic, Lady Rosetta and Dark Red Norland.

The phrase "effective to inhibit sprouting" means that: (a) the number, and/or the weight, of buds and sprouts/stems (sprouts) growing from a defined number of (potato) tubers contacted with a the carbonate ester formulation is less than the number, and/or the weight, of sprouts growing from the same number of control (potato) tubers (of the same cultivar as the treated (potato) tubers) that were not contacted with the carbonate ester formulation; and/or (b) the average rate of growth of buds, stems growing from a defined number of (potato) tubers contacted with the carbonate ester formulation is less than the average rate of growth of buds, stems growing from the same number of control (potato) tubers (of the same cultivar as the treated (potato) tubers) that were not contacted with the carbonate ester formulation. Such inhibition can be at any time as compared to the control. As understood by those in this field, the concept of inhibition is meaningful when control tubers show activity being inhibited in tubers contacted with the carbonate ester formulation in accordance with the invention. Another preferred measure of inhibition is a comparison between the total amount of "dormant or darkened bud or sprout tissue or bud or sprout tissue burned back compared to white healthy bud or sprout tissue, e.g. 24 hours after treatment up 4 weeks after treatment compared to untreated control. Whichever measure is used, preferred amounts of inhibition include less than 1%, 1%, 3%, greater than 3%, 5%, 8%, 10%, 20%, 30%, etc. to 100%.

The carbonate esters and other ingredients used herein can be purchased commercially, or synthesized or obtained based on existing literature. They (i.e., the carbonate esters, preferably alkylene carbonates, described herein and the carbonate ester formulations described herein) can be used alone or in mixture, and can be applied together with other materials such as other sprout inhibitors. By "together," we mean that they can be used in mixture with other materials such as active agents upon application to, e.g., potatoes, and/or can be used sequentially before, during, and/or after application of any other material.

In general, the present invention includes any application of a carbonate ester formulation containing at least one sprout inhibitor compound to tubers and or bulbs, and particularly includes application to potato plants in the field before the potatoes are harvested, and/or application after the potatoes are harvested but before they are stored, and/or application after the potatoes are in storage, and/or "on the line." In another preferred embodiment the carbonate ester formulation is applied via an aerosol, spray or thermal fog, to harvested potatoes. Methods of application also include via aerosol can and via smoke generators, for example for treatment in rail cars. The carbonate ester formulation compound may also be first or subsequently applied after tubers (potatoes) have been harvested and stored for a sufficient period that bruises and cuts have healed, i.e., suberization has occurred. In another aspect of the invention, the carbonate ester formulation is applied such that it inhibits sprouting during the potato shipping and distribution process and/or to burn back existing bud and/or sprout tissue and/or to inhibit sprouting of tubers.

In accordance with the foregoing, and in one embodiment, the present invention preferably provides methods for inhibiting sprouting during the potato shipping and distribution process and/or to burn back existing bud and/or sprout tissue and/or to inhibit sprouting of tubers, and maintain quality reducing shrink, the methods each including the step of contacting a potato tuber or a bulb with an amount of at least one carbonate ester formulation containing at least one sprout inhibitor compound wherein the amount of the formulation is effective to inhibit sprouting during the potato shipping and distribution process and/or to burn back existing bud and/or sprout tissue and/or to inhibit sprouting of tubers. Typically, the formulation is applied simultaneously, or substantially simultaneously, to numerous, harvested, potato tubers. In the practice of the methods of the invention the carbonate ester is typically applied after the potato tubers have been harvested, but typically not later than the onset of sprouting.

In a preferred embodiment of the invention, the carbonate ester formulation is applied after the potato tubers have been harvested, but typically not later than the onset of sprouting. Thus, in some embodiments of the methods of the invention, the carbonate ester formulation is applied to the tubers within one, two, three, four five, six, seven or eight weeks after the tubers are harvested. Typically, the carbonate ester formulation is applied before the end of the natural dormancy period of the harvested potato tubers, i.e., before the buds on the potato tubers have begun to sprout. In one embodiment the carbonate ester formulation is applied as close to the end of the natural dormancy period as is practical. The duration of the natural dormancy period is known to those of skill in the art and varies between potato cultivars, and depends on such factors as the physiology and condition of the tubers at harvest, and the storage temperature. For example, depending on temperature and potato cultivar estimates (in days) of the natural dormancy period falls between about 70-140 days at temperatures of 45-48° F.

If potatoes are subject to reconditioning, the carbonate ester formulation is typically applied at the beginning of the reconditioning period. Thus, in some embodiments of the invention, the carbonate ester formulation is applied one, two, three, four or five weeks before potato tubers are processed to make french fries or potato chips. In the practice of the methods of the invention, the carbonate ester formulation may be applied to the potato tubers on more than one occasion (e.g., at least twice) during the storage period.

In one embodiment, but not as a requirement, the carbonate ester formulation is applied simultaneously, or substantially simultaneously, to numerous, harvested, potato tubers stored in bulk storage sheds designed to hold anywhere from, e.g., 5000 to 25000 tons. The sheds are designed to precisely control ventilation through the bulk pile (which may be about twenty five feet deep) along with temperature and relative humidity. Temperature is controlled by refrigeration and/or ventilation with outside air through cell decks which also raises the humidity. For example, the carbonate ester formulation can be volatilized at high temperature and applied as a thermal fog into the storage ventilation system that circulates air through the potato pile, from bottom to top. The storage sheds are generally closed tight after fogging, and the air may be circulated internally through the pile for several hours after application of the carbonate ester formulation. Again by way of example, the carbonate ester formulation formulation can also be atomized or vaporized with various types of nozzles (e.g., air assisted, ultra-sonic or pressurized aerosol cans) or humidification apparatus to include centrifugal or cell decks and introduced onto the surface of one or more tubers via, e.g, the ventilation system of a storage sheds, or transit containers via humidification-type apparatuses such as humidifiers, drums, evaporators, filter pads, centripetal devices, and air assistance sprayers and via aerosol cans (smoke generators). The carbonate ester formulation can also be impregnated on filters, or other inert materials, to facilitate slow release over time through the ventilation system of the storage sheds. The carbonate ester formulation can also be applied as an emulsifiable concentrate for spraying onto fresh market potatoes as they go through sorting and packing lines prior to bagging.

The methods of the present invention are applicable to any potato cultivar including, but not limited to, Russet Burbank, Ranger Russet, Umatilla Russet, Shepody, Norkotah Russet, Yukon Gold, Norchip, Gem Russet, Atlantic, Chipeta, Snowden, Meris Piper, king Edward, Desiree, Atlantic, Lady Rosetta and Dark Red Norland.

The carbonate ester formulation can also be used in any way described for the treatment composition disclosed in U.S. Pat. No. 2007/0027033. In addition, the carbonate ester formulation of the present invention can contain, in addition, any of the active principles described in U.S. Pat.No. 2007/0027033 such as a salt of eugenol fit for human consumption, isoeugenol, a salt of isoeugenol fit for human consumption, etc. U.S. Pat No.2007/0027033 is incorporated herein by reference in its entirety. In this regard, a preferred method herein is an anti-germination method for bulbs and tubers including the application to said bulbs or tubers the carbonate ester formulation, said method including the application by sprinkling, spraying or immersion at, above or below ambient temperature of said carbonate ester formulation on the bulbs and tubers after storage.

EXAMPLES

The formulation was investigated for particle size and particle size distribution. The CIPC 98A product is a solid CIPC formulation in a briquette or pellet form. In the following Examples the solid product is added to Jeffsol AG-1555 material (propylene carbonate) in a melting tank in a ratio of 1:1 CIPC to Jeffsol AG-1555. The results are shown as follows, reflecting the average of two replicates:

This graph shows that as propylene carbonate is added to the CIPC product, a shift in particle size distribution is obtained. As can be observed, propylene carbonate consistently shifts the bulk of the particles to 3.4-4.5 microns. This reduction in particle size distribution obtained when the amount of propylene carbonate is increased results in better penetration of the formulation through the tuber pile and produces a more uniform distribution of the sprout inhibitor to the tubers. This even distribution results in a more uniform inhibition of potato sprouting, which is very important for commercial applications.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A composition to be applied to a potato tuber, comprising:
   at least one alkylene carbonate, and
   at least one sprout inhibitor,
   wherein the support inhibitor is at least one delected from the group consisting of chloropropham (CIPC), maleic hydrazide (MH), dimethylnaphthalene (DMN) and diisopropylnaphthalene (DIPN).

2. The composition according to claim 1, wherein the alkylene carbonate is at least one selected from the group consisting of ethylene carbonate, propylene carbonate, and butylene carbonate.

3. The composition according to claim 1, wherein the sprout inhibitor is a mixture of cloropropham (CIPC) and diisopropylnaphthalene (DIPN).

4. The composition of claim 1, wherein the alkylene carbonate is contained in an amount of from 10 to 99%, based on the total weight of the composition, and the sprout inhibitor is contained in an amount of from 1 to 90%, based on the total weight of the composition.

5. The composition of claim 1, wherein the alkylene carbonate is contained in an amount of from 20 to 99%, based on the total weight of the composition, and the sprout inhibitor is contained in an amount of from 1 to 80%, based on the total weight of the composition n.

6. The composition of claim 1, wherein the alkylene carbonate is contained in an amount of from 30-80%, based on the total weight of the composition, and the sprout inhibitor is contained in an amount of from 20-70%, based on the total weight of the composition.

7. A tuber comprising, on at least a part of a surface thereof, the composition according to claim 1.

8. A method, comprising applying the composition of claim 1 onto the surface of the tuber.

9. The method of claim 8 wherein the potato tuber is from a cultivar selected from the group consisting of Russet Burbank, Ranger Russet, Umatilla Russet, Shepody, Norkotah Russet, Yukon Gold, Norchip, Gem Russet, Atlantic, Chipeta, Snowden, Meris Piper, king Edward, Desiree, Atlantic, Lady Rosetta and Dark Red Norland.

10. The method of claim 8, comprising heating the composition to a temperature of from 40° C. to 240° C. prior to application.

11. A composition to be applied to a potato tuber, consisting of:
at least one alkylene carbonate , and
at least one sprout inhibitor,
wherein the support inhibitor is at least one delected from the group consisting of chloropropham (CIPC), maleic hydrazide (MH), dimethylnaphthalene (DMN) and diisopropylnaphthalene (DIPN).

12. A method of applying a sprout inhibitor to a tuber, the method comprising applying a formulation comprising at least one alkylene carbonate and at least one sprout inhibitor, which has been previously mixed, to a tuber,
wherein the support inhibitor is at least one delected from the group consisting of chloropropham (CIPC), maleic hydrazide (MH), dimethylnaphthalene (DMN) and diisopropylnaphthalene (DIPN).

13. The method of claim 12, wherein the alkylene carbonate is contained in an amount of from 10 to 99%, based on the total weight of the formulation, and the sprout inhibitor is contained in an amount of from 1 to 90%, based on the total weight of the formulation.

* * * * *